United States Patent [19]

Finch et al.

[11] Patent Number: 5,641,775
[45] Date of Patent: Jun. 24, 1997

[54] 3-PHENYLUREIDO-1,5-BENZODIAZEPINE-DIONES USEFUL AS GASTRIN OR ANTAGONISTS

[75] Inventors: Harry Finch, Hertfordshire, England; David Gordon Trist, Verona, Italy; Aldo Feriani, Verona, Italy; Giorgio Tarzia, Verona, Italy; Pritom Shah, Hertfordshire, Great Britain

[73] Assignee: Glaxo SpA, Verona, Italy

[21] Appl. No.: 532,811

[22] PCT Filed: Apr. 22, 1994

[86] PCT No.: PCT/EP94/01252

§ 371 Date: Oct. 23, 1995

§ 102(e) Date: Oct. 23, 1995

[87] PCT Pub. No.: WO94/25444

PCT Pub. Date: Nov. 10, 1994

[30] Foreign Application Priority Data

Apr. 23, 1993 [GB] United Kingdom ............... 9308431

[51] Int. Cl.$^6$ ............... A61K 31/55; C07D 243/12; C07D 403/12
[52] U.S. Cl. ............... 514/221; 540/518
[58] Field of Search ............... 540/518; 514/221

[56] References Cited

FOREIGN PATENT DOCUMENTS

| | | |
|---|---|---|
| 0376849 | 7/1990 | European Pat. Off. . |
| 0508796 | 10/1992 | European Pat. Off. . |
| 0538945 | 4/1993 | European Pat. Off. . |
| WO-A-9314074 | 7/1993 | WIPO . |
| WO94/25444 | 10/1994 | WIPO . |

*Primary Examiner*—Robert T. Bond
*Attorney, Agent, or Firm*—Bacon & Thomas

[57] ABSTRACT

The invention relates to 3-phenylureido-1,5-benzodiazepine-diones of formula (I)

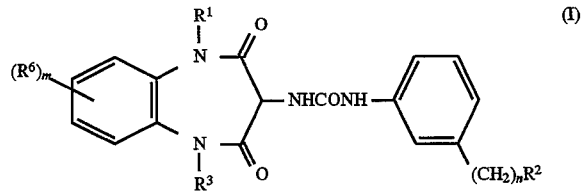

and pharmaceutically acceptable salts and solvates thereof, and to their use as gastrin/CCK-B antagonists.

10 Claims, No Drawings

3-PHENYLUREIDO-1,5-BENZODIAZEPINE-DIONES USEFUL AS GASTRIN OR ANTAGONISTS

This application is a 371 of PCT/EP 94/01252, filed 22 Apr. 1994.

This invention relates to novel 1,5-benzodiazepine derivatives, to processes for their preparation, to pharmaceutical compositions containing them and to their use in medicine.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxy terminal octapeptide, CCK-8 (also a naturally-occurring neuropeptide), and 39- and 12-amino acid forms. Gastrin occurs in 34-, 17- and 14-amino acid forms, with the miniumum active sequence being the C-terminal tetrapeptide, Trp-Met-Asp-Phe-$NH_2$ (CCK-4), which is the common structual element shared by both CCK and gastrin.

CCK and gastrin are gastrointestinal hormones and neurotransmitters in the neural and peripheral systems and perform their respective biological roles by binding to particular receptors located at various sites throughout the body.

There are at least two subtypes of cholecystokinin receptors termed CCK-A and CCK-B and both are found in the periphery and in the central nervous system. CCK and gastrin receptor antagonists have been disclosed for preventing and treating CCK-related and/or gastrin related disorders of the gastrointestinal and central nervous systems of animals, and more particularly humans.

U.S. Pat. No. 4,988,692 describes a group of 3-acylamino 1-alkyl-5-phenyl 1,5-benzodiazepine derivatives as cholecystokinin antagonists. Further the specification teaches that the compounds have a significantly greater affinity for the CCK-A receptor over the CCK-B receptor.

We have now found a novel group of 3-ureido 1,5-benzodiazepine compounds which are potent and specific antagonists of gastrin and/or CCK and in particular antagonists of gastrin and/or CCK at the CCK-B receptor.

Thus, the invention provides compounds of general formula (I)

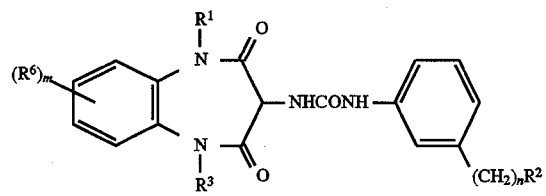

wherein $R^1$ represents a phenyl, $C_{3-7}$cycloalkyl, $C_{7-11}$ bridged cycloalkyl or $C_{1-6}$alkyl group which alkyl group may be substituted by a hydroxy, phenyl, $C_{1-6}$-alkoxycarbonyl, $C_{3-7}$cycloalkyl or $C_{7-11}$ bridged cycloalkyl group;

$R^2$ represents $NR^4SO_2CF_3$, $SO_2NR^4COR^5$, $CONR^4SO_2R^5$, or a tetrazole, carboxamidotetrazole, or 3-trifluoromethyl-1,2,4-trizole group which groups may be substituted on one of the nitrogen atoms by a $C_{1-4}$alkyl group;

$R^3$ is phenyl optionally substituted by one or two halogen atoms;

$R^4$ represents hydrogen or a $C_{1-4}$alkyl group;

$R^5$ represents a $C_{1-4}$alkyl group;

$R^6$ represents hydrogen or a halogen atom; m is zero, 1 or 2;

n is zero or 1; and pharmaceutically acceptable salts and solvates thereof.

It will be appreciated that compounds of formula (I) possess at least one asymmetric carbon atom (namely the carbon atom occupying the 3-position of the diazepine ring) and the compounds of the invention thus include all stereoisomers and mixtures thereof including the racemates.

In the compounds of formula (I) 'alkyl' when used as a substituent or part of a substituent group means that the group may be straight or branched. Thus, $C_{1-6}$ alkyl includes methyl, ethyl, n-propyl, isopropyl, n-butyl, isobutyl or tert-butyl, n-pentyl, isopentyl neopentyl, n-hexyl, isohexyl, 1,3-dimethylbutyl, 3,3-dimethylbutyl, 2,3-dimethylbutyl.

For the group $R^1$ the term $C_{3-7}$ cycloalkyl as a group or part of a group refers to a monocyclic alkyl group such as cyclopropyl, cyclobutyl, cyclopentyl, cyclohexyl or cycloheptyl. The term $C_{7-11}$ bridged cycloalkyl as a group or part of a group refers to groups such as adamantyl, norbornanyl or norbornenyl.

For the groups $R^4$, $R^5$ and $R^7$ (below) the term $C_{1-4}$alkyl includes 3-4 cycloalkyl (e.g. cyclopropyl or cyclobutyl) as well as straight or branched chain alkyl groups as defined above.

When $R^2$ represents a tetrazole group suitable examples include

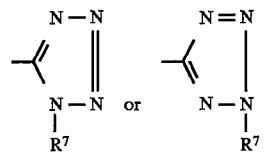

When $R^2$ represents a carboxamidotetrazole grouping suitable examples include

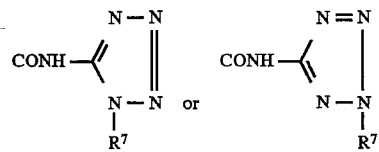

When $R^2$ represents a 3-trifluoromethyl 1,2,4-triazole grouping suitable examples include

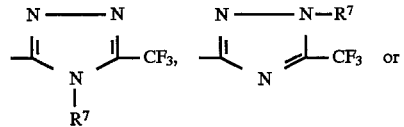

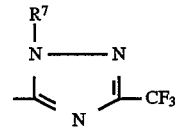

The group $R^7$ represents hydrogen or a $C_{1-4}$alkyl group. It will be appreciated that when $R^7$ represents a hydrogen atom the various isomers for each heterocyclic group are tautomers of that heterocyclic group and all tautomers are included where the formula shows a single tautomer.

When $R^6$ is halogen this is preferably chlorine or fluorine.

When m is 1 or 2 the halogen atom(s) e.g. chlorine or fluorine are preferably in the 7 and/or 8 position.

Halogen in the definition of compounds of formula (I) may represent a fluoro, chloro, bromo or iodo substituent.

A preferred class of compounds of formula (I) is that in which $R^1$ represents a phenyl, phenethyl, methyl, $C_{4\text{-}6}$ alkyl e.g. n-butyl, 3-methyl-butyl, 3,3-dimethylbutyl, 1,3-dimethylbutyl, 2,3-dimethylbutyl, $C_{3\text{-}6}$ hydroxyalkyl e.g. 2-hydroxypropyl, 2-hydroxy-3-methylbutyl, 2-hydroxy-3,3-dimethylbutyl, $C_{1\text{-}2}$ alkyl substituted by a bridged $C_{7\text{-}10}$ cycloalkyl group e.g. 2-norbornanylmethyl 5-norbornenylmethyl, 1-adamantylethyl, 1-adamantylmethyl, alkoxycarbonylalkyl, (e.g. methoxycarbonylmethyl or t-butyoxycarbonylmethyl), or 2-cyclopentylethyl.

A particularly preferred class of compounds of formula (I) is that in which $R^1$ is 3-methyl-butyl, 3,3-dimethylbutyl, 2-hydroxy-3,3-dimethylbutyl, 1-adamantylmethyl, 2-cyclopentylethyl or 5-norbornenylmethyl. A further preferred class of compounds of formula (I) is that in which $R^2$ represents $NHSO_2CF_3$, $SO_2NHCOCH_3$, $CONHSO_2CH_3$,

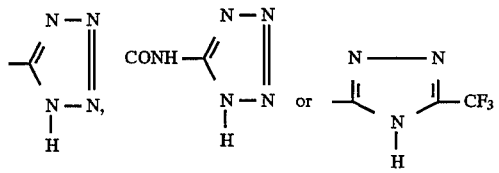

Most preferably $R^2$ represents

(1H-tetrazol-5-yl)

A further preferred class of compounds of formula (I) is that wherein n is zero.

When m is 1 or 2 preferred compounds are those wherein $R^6$ is chlorine or fluorine in the 7 and/or 8 positions.

A further preferred class of compounds of formula (I) is that in which $R^3$ represents phenyl or phenyl mono- or di-substituted by fluorine, preferably in the ortho and/or para position(s). Preferably $R^3$ represents unsubstituted phenyl or 2-fluorophenyl.

A further preferred class of compounds of formula (I) is that wherein m is zero.

A particularly preferred group of compounds of the invention are those wherein $R^1$ is 3-methylbutyl, 3,3-dimethylbutyl or cyclopentylethyl, $R^2$ represents 1H-tetrazole-5-yl, $R^3$ represents phenyl or 2 fluorophenyl and n and m are zero.

Preferred compounds according to the invention include:
N-[1-(Cyclopentylethyl)-2,4-dioxo-5-(2-fluorophenyl)-2,3,4,5-tetrahydro-1H-benzodiazepin-3-yl]-N'-(3-tetrazolyl)phenylurea;
N-[2,3,4,5-Tetrahydro-1-(3-methylbutyl)-2,4-dioxo-5-phenyl-1H-1,5-benzodiazepin-3-yl]-N'-[3-(1H-tetrazol-5-yl)phenyl]urea;
N-[1-(3,3-Dimethylbutyl)-2,4-dioxo-5-phenyl-2,3,4,5-tetrahydro-1H-1,5-benzodiazepine-3-yl]-N'[3-(5-tetrazolyl)-phenyl]urea, enantiomers and salts thereof.

The pharmaceutically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

References hereinafter to a compound according to the invention includes both compounds of formula (I) and their pharmaceutically acceptable salts and solvates.

The compounds of the invention are potent and specific antagonists of gastrin and/or CCK. The compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

The compounds of the invention have also been shown to be antagonists of gastrin as demonstrated by their ability to inhibit pentagastrin-stimulated acid secretion from rat isolated gastric mucosa using the procedure described by J. J. Reeves and R. Stables in Br. J. Pharmac. 1985, 86, p.677–684.

Compounds of the invention have also been found to have a significantly weaker activity at CCK-A receptors compared with their activity at gastrin and/or CCK-B receptors, as demonstrated by their ability to inhibit the contractile activity of CCK-8 in guinea-pig isolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol, (1985), 329, p36–41 and by V. L. Lucaites et al (1991) in J. Pharmacol. Exp. Ther., 256,695–703.

The greater affinity of the compounds of the invention for the CCK-B receptor over the CCK-A receptor has also been established using the CCK receptor binding assays described by G Dal Fornos et al., J. Pharmcol. Exp & Ther. 261, 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), tardive dyskinesia, depression, Parkinson's disease or psychosis. The compounds of the invention are also useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. They may also be useful for the treatment of dependency on drugs or substances of abuse and withdrawal, Gilles de la Tourette syndrome, or dysfunction of appetite regulatory systems; as well as the treatment of certain tumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 20–2000 mg per day e.g. 100–500 mg per day.

The desired dose may conveniently be presented in a single dose or as divided doses administered at appropriate intervals, for example as two, three, four or more sub-doses per day.

Because the compounds of the invention antagonise the function of CCK in animals, they may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients, The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Compounds of general formula (I) and salts thereof may be prepared by the general methods outlined hereinafter. In the following description, the groups $R^1$–$R^7$ are as defined for the compounds of formula (I) unless otherwise stated.

According to a first general process (A) compounds of formula (I) may be prepared by reacting a compound of formula (II) in which X represents the group —N=C=O, or NHCOR$^8$ wherein R$^8$ is a phenoxy or 1-imidazole group.

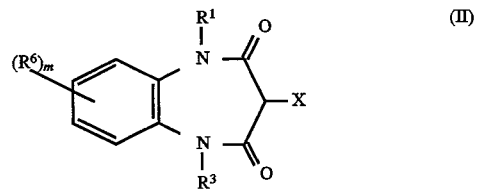

with an aniline of formula (III)

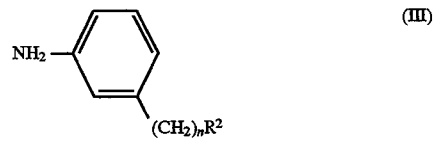

optionally in the presence of a base such as a tertiary amine (e.g. triethylamine). The reaction conveniently takes place in a suitable solvent such as a halogenated hydrocarbon (e.g. dichloromethane) or an ether (e.g. tetrahydrofuran) or an amide e.g. N,N-dimethylformanide optionally at a temperature ranging from room temperature to the reflux temperature of the solvent.

In a particular aspect of the process (A) when X is the group NHCOR$^8$ and R$^8$ is a 1-imidazole group the imidazolide (II) may be formed in situ in which case the aniline of formula (III) will be mixed with a compound of formula (IV)

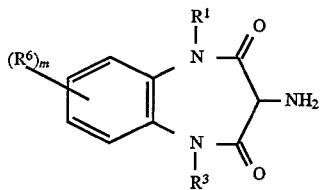

in the presence of carbonyldiimidazole under the aforementioned conditions.

The compounds of formula (II) wherein $R^8$ is phenoxy group may be prepared from the primary amine (IV) by reaction with phenyl chloroformate in the presence of a base such as pyridine. The reaction may be carried out in a solvent such as a halohydrocabon e.g. dichloromethane and at a temperature from 0°–50°.

Compounds of formula (II) wherein $R^8$ is a 1-oimidazole group may be prepared by reacting a compound of formula (IV) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

Compounds of formula (II) wherein X is the isocyanate grouping —N=C=O may be prepared from the primary amine (IV) by reaction with phosgene ($COCl_2$) in a suitable solvent such as methylene chloride.

According to a further general process (B) compounds of formula (I) may be prepared by reacting a compound of formula (IV) with an isocyanate of formula (V)

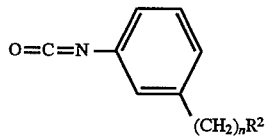

or a carbamoyl chloride of formula (VI)

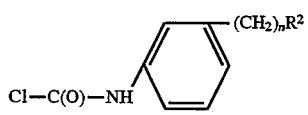

The reaction conveniently takes place in the presence of a suitable solvent such as a halohydrocarbon (e.g. dichloromethane), an ether (e.g. tetrahydrofuran) or a nitrile (e.g. acetonitrile) or a mixture thereof at a temperature in the range of 0° C. to 80° C.

In a modification of this process the amine (III) may be reacted with triphosgene in the presence of triethylamine and in a solvent such as an ether e.g. tetrahydrofuran and the product thus obtained reacted with the amine (IV) to yield a compound of formula (I).

Compounds of formula (IV) may be prepared by reduction of compounds of formula (VII)

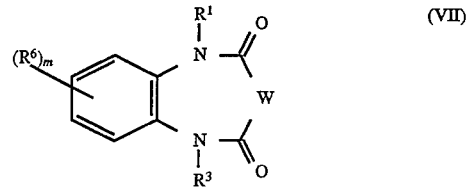

wherein W is CH—$N_3$ or C=N—NHPh.

Compounds of formula (VII) wherein W is CH—$N_3$ may be reduced to a compound of formula (IV) by hydrogenation in the presence of a suitable catalyst such as palladium on carbon or platinum (IV) oxide. The reaction conveniently takes place in the presence of a solvent such as an alkanol (e.g. ethanol) an ester (e.g. ethyl acetate) or acetic acid.

Compounds of formula (VII) wherein W is C=N—NHPh may be reduced to a compound of formula (IV) by reaction with zinc and acetic acid. This reaction may be carried out a temperature with the range 0°–50°.

Compounds of formula (VII) wherein W is $CHN_3$ may be prepared from a compound of formula (VII) wherein W is $CH_2$ by treatment with a strong base such as sodium hydride or potassium tert-butoxide followed by tri-isopropyl benzenesulphonyl azide. The reaction conveniently takes place in a solvent such as an ether (e.g. tetrahydrofuran) at a temperature in the range of −78° to 20°.

Compounds of formula (VII) in which W is C=NNHPh may be prepared by reaction of the ortho-phenylenediamine (VIII) with the diacid chloride (IX), in a suitable solvent such as an ether e.g. tetrahydorfuran

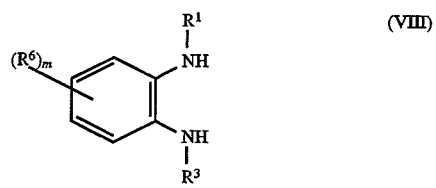

Compounds of formula (VII) wherein W is $CH_2$ prepared by reaction of the corresponding compound (X)

with a compound $R^1Y$ where Y is halogen (e.g. a chlorine or bromine atom) or a mesylate group under strongly basic conditions. Thus the reaction may conveniently be carried out by pretreating the compound of formula (X) with a strong base such as sodium hydride in a suitable aprotic solvent such as an amide (e.g. N,N-dimethylformamide) at a temperature ranging from 0° to reflux. In the above described reaction scheme when the group $R^1$ contains an hydroxyl group then this may be present in a protected form e.g. as an ether such as an arylmethyl ether e.g. a benzyl ether.

Compounds of formula (VIII) are either known compounds or may be prepared by analogous methods. Thus for example a compound of formula (VIII) may be prepared by alkylation of the amine (XI).

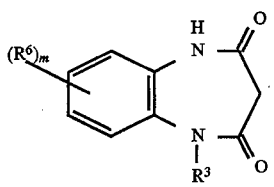

Thus the amine (XI) may be reacted with the compound $R^1Y$, in which Y is chlorine or bromine, optionally in the presence of sodium iodide in a solvent such as N,N-dimethylformamide.

Compounds of formula (VIII) wherein $R^1$ represents the group $—CH_2—CH(OH)R^1_a$ where $R^1_a$ is a $C_{1-4}$alkyl group may be prepared by reaction of compound (XI) with the epoxide (XII) in a solvent such as an alkanol e.g. ethanol and in the presence of an acid catalyst such as p-toluene sulphonic acid.

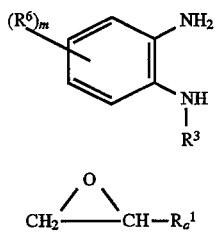

Compounds of formula (VIII) where in $R^1$ is an optionally substituted alkyl group. May also be prepared from compound (XI) by reaction with a suitable aldehyde or ketone with concomitant or subsequent reduction of the reaction product. Thus for example a compound formula (VIII) wherein $R^1$ is 2-(4-methylpentyl) may be prepared from compound (XII) by reaction with methylisobutyl ketone followed by reaction with sodium borohydride.

In general, the anilines of formula (III) will be known or may be prepared according to methods used for the preparation of known compounds, for example they may be prepared by reduction of the corresponding nitro compounds. Reduction may be effected for example by catalytic hydrogenation using a suitable metal catalyst such as palladium on carbon in a suitable solvent such as an alcohol e.g. ethanol) at room temperature.

In the processes described above the group $R^2$ in the intermediates III, V and VI may be a group as defined in formula (I) or a group convertible thereto. Thus compounds of formula (I) wherein $R^2$ represents an unsubstituted tetrazole grouping may be prepared from the corresponding compounds of formula (I) when $R^2$ represents a nitrile group by reaction with a trialkylbutyl tinazide such as tributyltinazide. The reaction is preferably carried out with heating and in an inert atmosphere e.g. under nitrogen.

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as salt formation with a suitable optically active acid or by the use of chiral HPLC. Alternatively the required enantiomer may be prepared by the corresponding enantiomeric amine of formula (IV) using any of the processes described above for preparing compounds of formula (I) from the amine (IV). The enantiomers of the amine (IV) may be prepared from the racemic amine (IV) using conventional procedures such as salt formation with a suitably optically active acid.

The following examples, which are non-limiting, illustrate the invention. Temperatures are in °C. "Dried" refers to drying with anhydrous $MgSO_4$. All chromatography was carried out on silica gel. The following abbreviations are used. T.l.c.—thin layer chromatography; CDI—carbonyldiimidazole; TEA—triethylamine; THF—tetrahydrofuran; HCl—hydrochloric acid; EA—ethyl acetate; DE—diethyl ether; EtOH—ethanol; MeOH—methanol; DMF—N,N-dimethylformamide; DMSO—dimethyl sulfoxide (deuterated for N.m.r's); $CDCl_3$-deuterochloroform; DCM—dichloromethane; KO$^t$Bu—potassium tert-butoxide.

INTERMEDIATE 1

$N^2$-(3-Methylbutyl)-$N^2$-phenyl-1,2-benzenediamine 1-iodo-3-methylbutane (14.9 g) was added to a mixture of 2-aminodiphenylamine (27.6 g) and potassium carbonate (20.7 g) in dry DMF (150 ml) at 23° under nitrogen. After 2 h the mixture was heated to 60° for 24 h. The cooled mixture was filtered and the flitrate evaporated. The residue was chromatographed with hexane-EA (9:1) as eluent to give the title compound (12.5 g) as a brown oil.

T.l.c. hexane-EA (19:1) Rf 0.44

IINTERMEDIATE 2

1-(3-Methylbutyl)-5-phenyl-1H-1,5-benzodiazepine-2,3,4-(5H)-trione-3-(phenylhydrazone)

Solutions of $N^1$-(3-Methylbutyl)-$N^2$-phenyl-1,2-benzenediamine (12.45 g) in dry THF (100 ml) and (phenylhydrazono)propandioyl dichloride (12.0 g) in dry THF (100 ml) were added dropwise concurrently to a flask of dry THF (100 ml) cooled in an ice-methanol bath under nitrogen. After 30 min more diacid chloride (1.0 g) in dry THF (30 ml) was added and the mixture was allowed to warm to 23°. After 24 h the mixture was poured into dilute HCl and extracted with EA. The combined extracts were washed with dilute sodium carbonate and saturated brine then dried and evaporated. The residue was chromatographed on TEA deactivated silica with EA as eluent to give the title compound (20.2 g) as a yellow solid, m.p. 143°

T.l.c. Hexane-EA (2:1) Rf 0.45.

INTERMEDIATE 3

3-Amino-1-(3-methylbutyl)-5-phenyl-1H-1,5-benzodiazepine-2,4-(3H,5H)-dione

Zinc dust (26 g) was added to a suspension of 1-(3-methylbutyl)-5-phenyl-1H-1,5-benzodiazepine-2,3,4-(5H)-trione 3-(phenylhydrazone) (20.2 g) in 97% acetic acid (260 ml) at 23° under nitrogen. After 1 h the mixture was filtered and the filtrate evaporated. The residue was redissolved with DCM (200 ml) and water (100 ml) and the mixture was cautiously neutralised by portionwise addition of solid sodium carbonate. The mixture was extracted with DCM and the combined organic extracts were washed with saturated brine, dried and evaporated. The residue was chromatographed with DCM-MeOH (1→8%) as eluent to give the title compound (11.9 g) as a yellow oil.

T.l.c. MeOH-DCM: (1:9) Rf 0.54

INTERMEDIATE 4

N-[2,3,4,5-Tetrahydro-1-(3-methylbutyl)-2,4-dioxo-5-phenyl-1H-1,5-benzodiazepin-3-yl]-1H-imidazole-1-carboxamide CDI (481 mg) was added to a solution of 3-Amino-1-(3-methylbutyl)-5-phenyl-1H-1,5-benzodiazepine-2,4-(3H, 5H)-dione (1.0 g) in dry DCM (10 ml) at 23° under nitrogen. After 5 h the mixture was evaporated then redissolved in EA and was washed with water and saturated brine. The combined organic extracts were dried and evaporated to give the title compound (1.14 g) as a yellow foam, m.p. 62°–65°.

T.l.c. 5% MeOH in DCM Rf 0.21

INTERMEDIATE 5

N-(3-cyanophenyl)-1H-imidazole-1-carboxamide

3-Aminobenzonitrile (2.0 g) and CDl (2.75 g) were dissolved in dry DCM (20 ml), and the resulting mixture stirred under nitrogen for 1 h. After about 30 min the clear yellow solution went cloudy and a white solid was precipitated. The mixture was filtered, washed with DCM and dried in vacuo to give the title compound (3.13 g) as a white solid m.p. 174°–176°.

$H^1$NMR δ(DMSO) 7.0 (1H,s); 7.45–7.75 (4H,m); 8.0 (1H,s), 9.25 (1H,s), 12.0 (1H,bs).

INTERMEDIATE 6

3-Diazo-1-methyl-5-phenyl-1H-1,5-benzodiazepine-2,4(3H,5H)-dione

A solution of 1-methyl-5-phenyl-1H-1,5-benzodiazepin-2,3(3H,5H-dione (1.25 g) in THF (19 ml) and DMF (1 ml) at 0° under nitrogen was treated with sodium hydride (80%, 0.155 g). After stirring at room temperature for 30 min a solution of p-toluenesulphonylazide (0.925 g) in THF (2.5 ml) was added and the mixture stirred at room temperature for 4 h. Filtration and evaporation gave a residue which was dissolved in EA, washed with brine, dried and evaporated to give the title compound as a yellow glass (1.30 g), T.l.c. EA-Hexane (50:50), Rf 0.82; $H^1$NMR (CDCl$_3$) 7.5–7.1 (9H,m); 3.5 (3H,s)

INTERMEDIATE 7

3-Amino-1-methyl-5-phenyl-1H-1,5-benzodiazepine-2,4(3H,5H)-dione

A solution of Intermediate 6 (0.680 g) in acetic acid (50 ml) and water (20 ml) was hydrogenated over 5% palladium on carbon (0.30 g) for 5.5 h at NTP. The solvent and catalyst were removed and the residue partitioned between aqueous sodium bicarbonate (8%) and DCM. The organic extract was washed with brine and dried. Evaporation gave a residue which on purification by CC using DCM-MeOH (97:3) as eluent gave the title compound as a glass (0.292 mg), T.l.c. DCM-MeOH (95:5), Rf 0.36; $_{max}$ (CHB5$_3$) 3377, 3314, 1704, 1668 cm$^{-1}$

INTERMEDIATE 8

N-(3-cyanophenyl)-N'-(2,3,4,5-tetrahydro-2,4-dioxo-1-methyl-5-phenyl-1H-1,5-benzodiazepin-3-yl)urea 3-Amino-1-methyl-5-phenyl-2,3,4,5-tetrahydro-2,4-dioxo-1H-1,5-benzodiazepine (360 mg) was suspended in dry THF (10 ml) under nitrogen. N-(3-cyanophenyl)-1H-imidazole-1-carboxamide (326 mg) was added, and the mixture stirred at room temperature for 2 h. The mixture was filtered to give the title compound (510 mg) as a white solid m.p.>250°.

$H^1$NMR (DMSO) 3.5 (3H,s); 5.1 (1H,d); 7.0 (1H,dd); 7.1 (1H,d); 7.25–7.6 (10H,M); 7.75 (1H,d); 7.95 (1H,s); 9.6 (1H,s).

INTERMEDIATE 9

1-(3,3-Dimethylbutyl)-2,4-dioxo-5-[phenyl2,3,4,5-tetrahydro-1H,1,5-benzodiazepine Sodium hydride 80% dispersion in oil (0.100 g) was added portionwise to a solution of 5-phenyl-1H-5,5-benzodiazepine-2,4 (3H,5H)-dione (0.7 g)in DMF (60 ml). The reaction mixture was stirred for 30 min, then a solution of 3,3-dimethylbutyl methanesulfonate (0.575 g) in DMF (3 ml) was added. The reaction mixture was stirred at 90° C. for 50 min, at 23° C. for 15 hrs, at 90° C. for 2 hrs and at 140° C. for 45 min, then concentrated. The residue was diluted with water (30 ml) and brin (20 ml) and extracted with EA (150 ml); the organic layer was washed with water (2×50 ml) and brine (50 ml) dried and concentrated "in vacuo". The crude product was purified by flash chromatography (eluting with CH-EA 1:1) to give the title compound as a white foam (0.4 g).

T.l.c. CH-EA (1:1), Rf=0.39. IR: 1713 (C=O), (C=C) cm–1;

$^1$H-NMR: 7.48–7.08 (m) 6.95(dd), 4.60–4.40(m), 3.7–3.55(m), 3.49(s), 1.52–1.40(m), 0.95(s).

INTERMEDIATE 10

3-Azido-1-(3,3-dimethylbutyl)2,4-dioxo-5-phenyl-2,3,4,5-tetrahydro-1H,-1,5-benzodiazepine A solution of potassium tert-butoxide (0.146 g) in THF (7 ml), cooled to –70° C. was added dropwise to a solution of the intermediate 9 (0.4 g) in THF (15 ml), cooled to –70° C. under a nitrogen atmosphere. The solution was stirred for 20 min at –70° C. then a solution of 2,4,6-triisopropylbenzenesulphonuyl azide (0.530 g) in THF (7 ml) previously cooled to –70° C. and acetic acid (0.139 ml) were added. The reaction mixture was allowed to stand at 23° C. and stirred for 18 hrs, then EA (75 ml) was added and the solution was washed with water (2×50 ml) and brine (2×30 ml), dried and concentrated "in vacuo". The crude product was purified by flash chromatography (eluting with CH-EA 30:70) to give the title compound as a white foam (0.338 g)

T.l.c. CH-EA (1:1) Rf=0.73.IR: 2127(N$_3$), 1693, 1666 (C=O), 1597(C=C)cm$^{-1}$;

$^1$H-NMR: 7.44–7.40(m), 7.38–7.31(m), 7.24–7.17(m), 6.999(dd), 4.537–4.434(m), 4.20(s), 3.775–3.674(m), 1.523 (m), 0.967(s).

INTERMEDIATE 11

3-Amino-1-(3,3-dimethylbutyl)2,4-dioxo-5-phenyl-2,3,4,5-tetrahydro-1H-1,5-benzodiazepine A solution of the intermediate 10 (0.298 g) in a mixture of EtOH (18 ml) and EA (7 ml) was stirred under hydrogen, at 1 atm., in presence of 5% Pd/CaCO$_3$ (0.186 g) at 23°C., for 1½ hrs, then more 5% Pd/CaCO$_3$ (0.180 g) was added and the reaction stirred for 1 hrs. The catalyst was filtered off on a pad of celite, washing with EtOH (20 ml) and the organic layer was concentrated "in vacuo". The crude product was purified by flash chromatography (eluting with DCM-MeOH 90:10) to give the title compound as a white foam (0.205 g).

T.l.c. DCM-MeOH (90:10), Rf=0.46. IR: 1701, 1670 (C=O), 1593 (C=C)cm$^{-1}$;

$^1$H-NMR: 7.47–7.12(m), 6.91(dd), 4.58–4.40(m), 3.80–3.63(m), 4.24(s), 1.54–1.45(m), 1.85–1.55(m), 0.96(s).

INTERMEDIATE 12

1-(3,3-Dimethylbutyl)-2,4-dioxo-3-isocyanato-5-phenyl-2,3,4,5-tetrahydro-1H,1,5-benzodiazepine To a solution of the intermediate 11 (0.3 g) in DCM (20 ml) a 1.93M solution of $COCl_2$ in toluene (10 ml) was added. The reaction mixture was stirred for 5 hrs at 23° C. then concentrated "in vacuo" at 50° C. for 3 hrs to obtain the title compound as a white foam (0.370 g). IR: 2218 (N═C═O); 1693, 1668 (C═O), (C═C)cm$^{-1}$;

$^1$H-NMR: 7.48–7.18(m), 7.01(ddO, 4.57(s), 4.54–4.42 (m), 3.80–3.68(m), 1.60–1.46(m),0.96(s).

INTERMEDIATE 13

Cyclopentylacetic Acid, Methyl Ester

Thionyl chloride (7.0 ml) was slowly added to a solution of cyclopentylacetic acid (8.0 ml) in dry methanol (60 ml) and the mixture was stirred at 23° for 20 h. The mixture was concentrated in vacuo; then, the residue was taken up in DCM (100 ml), washed with a 5% sodium bicarbonate solution (50 ml), water (50 ml) and brine (50 ml), dried and concentrated in vacuo to give the title compound (6.47 g) as a yellow oil, which was not purified further. T.l.c. CH-EA (1:1), $R_f$=0.79. $^1$H-NMR: 3.70(s); 2.35(s); 2.4–2.15(m); 1.8(m); 1.7–1.5(m); 1.2(m).

INTERMEDIATE 14

Cyclopentylacetaldehyde

Diisobutylaluminum hydride, 1M solution in toluene, (45.5 ml) was slowly added to a cooled (−78° C.) solution of intermediate 13 (6.47 g) in dry dichloromethane (150 ml). The mixture was stirred at −78° C., under a nitrogen atmosphere, for 1 h, then it was quenched with cold methanol (2 ml) and a saturated ammonium chloride solution (57 ml). Water (50 ml) was added and the resulting aluminum hydroxide precipitate was filtered off; the solution was concentrated in vacuo at 30° C. to a small volume, to give the title compound (5.10 g), which was not further purified or characterized, but was directly used, as dichloromethane solution, in the preparation of intermediate 17. T.l.c. CH:EA (8:2), $R_f$=0.67.

INTERMEDIATE 15

N-(2-Fluorophenyl)-2-nitrobenzeneamine

A mixture of 2-fluoroaniline (13.0 ml), 2-fluoronitrobenzene (14.2 ml) and potassium iodide (5.5 g) was heated at 180° for 18 h. The mixture was cooled to 23° C.; the solid materials were filtered off and the solution was concentrated in vacuo. The residue was purified by flash chromatography (eluting with CH-EA 7:3) then crystallized from absolute ethanol to give the title compound as an orange solid (9.30 g). T.l.c. CH-EA (7:3), $R_f$=0.69. M.p. 76°–77° C. IR: 3352 (NH), 1609 (C═C), 1510 and 1350 ($NO_2$) cm$^{-1}$.

INTERMEDIATE 16

N-(2-Fluorophenyl)-1,2-benzenediamine

A solution of potassium carbonate (20.7 g) and sodium hydrosulfite (27.7 g) in water (180 ml) was added dropwise to a solution of intermediate 15 (9.24 g) in ethanol (270 ml). The mixture was stirred at 23° for 1 h, then the solid materials were filtered off through a pad of celite and the solution was acidified with conc. hydrochloric acid until pH=3. The mixture was concentrated to half volume then basified with a 10% sodium hydroxide solution until pH=10. The residue was extracted with ethyl acetate (2×250 ml); the combined extracts were washed with a saturated ammonium chloride solution (200 ml) and brine (200 ml), dried and concentrated in vacuo to give the title compound as a brown solid (8.25 g). T.l.c. CH-EA (10:1), $R_f$=0.27. M.p. 82°–3°. IR: 3490 and 3412 (NH), 1630 (C═C) cm$^{-1}$.

INTERMEDIATE 17

N-(Cyclopentylethyl)-N'-(2-fluorophenyl)-1,2-benzenediamine

A solution of sodium acetate (16.2 g) and glacial acetic acid (25 ml) in water (70 ml) was added to a mixture of intermediate 14 (5.10 g) and intermediate 16 (8.25 g) in ethanol (75 ml), kept at 0°. More ethanol (100 ml) was added, then sodium borohydride (22.6 g) was added portionwise, over 30 min., always keeping the mixture at 0° C. After stirring for 2 h, the mixture was diluted with ethyl acetate (250 ml), washed with water (300 ml), 10% sodium hydroxide solution (2×300 ml) and water (300 ml), dried and concentrated in vacuo. The residue was purified by flash chromatography (eluting with CH:EA from 100:0 to 90:10) to give the title compound as an orange oil (3.44 g). T.l.c. CH-EA (9:1), Rf=0.78. IR: 3398 (NH); 1618–1605 (C═C) cm$^{-1}$.

INTERMEDIATE 18

1Cyclopentylethyl-2,4-dioxo-5-(2-fluorophenyl)-3-phenylhydrazono-2,3,4,5-tetrahydro-1H-1,5-benzodiazepine A solution of the intermediate 17 (3.44 g) in ethyl acetate (200 ml) was added, dropwise, to a solution of 2-phenylhydrazonomalonyldichloride (3.10 g) in ethyl acetate (200 ml) at 23° under a nitrogen atmosphere. After complete addition the solution was stirred for 1 h, then heated at 50° for 1 h. The solution was cooled to 23°, washed with a 10% sodium hydroxide solution (300 ml) and brine (300 ml). The organic layer was dried, concentrated in vacuo and the residue was purified by flash chromatography (eluting with CH-EA 6:4) to give the title compound as a yellow foam (3.37 g). T.l.c. CH-EA (1:1 ), $R_f$ 0.52. IR: 3250 (NH); 1670=1659 (C═O); 1610–1595 (C═C) cm$^{31\ 1}$.

INTERMEDIATE 19

3-Amino-1-cyclopentylethyl-2,4-dioxo-5-(2-fluorophenyl)-2,3,4,5-tetrahydro-1H-1,5-benzodiazepine Ammonium formate (4.54 g) and 10% palladium on charcoal (3.21 g) were added to a solution of intermediate 18 (3.37 g) in dry methanol (140 ml) and the mixture was refluxed, under a nitrogen atmosphere, for 30 min. Then, the mixture was filtered over celite; the flitrate was concentrated in vacuo, taken up in diethyl ether (100 ml) and extracted with a 10% hydrochloric acid solution (100 ml). The aqueous phase was neutralized with solid sodium bicarbonate, then extracted with ethyl acetate (2×200 ml). The organic layer was washed with brine (200 ml), dried and concentrated in vacuo to give the title compound, (2.76 g) as a light yellow oil. T.l.c. DCM:MeOH (99:1), Rf=0.36. IR: 1709 and 1672 (C═O); 1597 (C═C) cm$^{-1}$.

INTERMEDIATE 19a,

3-Amino-1-cyclopentylethyl-2,4-dioxo-5-(2-fluorophenyl)-2,3,4,5-tetrahydro-1H-1,5-benzodiazepine Isomer 1

A solution of intermediate 19 (2.0 g) in ethyl acetate (16 ml) was heated at 90°, then, (1R)-(−)-camphorsulphonic acid (1.10 g) was added and heating was continued for 5 min. More ethyl acetate (8 ml) was added, then the solid formed was filtered; its mother liquors were concentrated to dryness and used directly in the preparation of the following intermediate 19b. The solid was instead treated as follows: it was dissolved in dichloromethane (20 ml), washed with a 5% ammonia solution (20 ml), water (20 ml) and brine (20 ml), dried and concentrated in vacuo to give a light yellow foam. This material was dissolved in ethyl acetate (9 ml) and treated again with R-(−)-camphorsulphonic acid (0.41 g), at 90° for 5 min., to give a salt which was recrystallized from hot isopropanol. The resulting salt was dissolved in dichloromethane (20 ml), washed with a 5% ammonia solution (20 ml), water (20 ml) and brine (20 ml), dried and concentrated in vacuo to give the title compound (0.558 g) as a white foam. The enantiomeric ratio of compound 19a was determined by chiral HPLC of the corresponding phenylurea and was found to be 1.3/98.7. T.l.c. DCM:MeOH (99:1), Rf=0.36.

IR: 1709 and 1672 (C═O); 1597 (C═C) cm$^{-1}$. 1H NMR: 7.43 (dd); 7.4–7.14 (m); 6.95 (dd); 4.46 (m); 4.28 (s); 3.69 (m); 2.2 (m); 1.9–1.4 (m); 1.3–1.0 (m).

INTERMEDIATE 19b

3-Amino-1-cyclopentylethyl-2,4-dioxo-5-(2-fluorophenyl)-2,3,4,5-tetrahydro-1H-1,5-benzodiazeoine Isomer 2

The mother liquors obtained from the preparation of the above intermediate 19a, were dissolved in dichloromethane (40 ml), washed with a 5% ammonia solution (40 ml), water (40 ml) and brine (40 ml), dried and concentrated in vacuo to a residue (1.24 g) containing an enriched mixture of amines 19a and 19b. A solution of this material in ethyl acetate (10 ml) was heated at 90°; then, S-(+)-camphorsulphonic acid (0.68 g) was added and heating was continued for 25 min. The mixture was then kept at 23° for 2 h. The precipitate formed was filtered, dissolved in dichloromethane (30 ml), washed with a 5% ammonia solution (30 ml), water (30 ml) and brine (30 ml), dried and concentrated in vacuo to give a white foam. This material was redissolved in ethyl acetate (4 ml) and treated again with S-(+)-camphorsulphonic acid (0.292 g) at 90° for 10 min. The precipitate formed was filtered and recrystallized from ethyl acetate, then from isopropanol. The resulting salt was dissolved in dichloromethane (30 ml). washed with a 5% ammonia solution (30 ml), water (30 ml) and brine (30 ml), dried and concentrated in vacuo to give the title compound 19b (0.144 g) as a white foam. The enantiomeric ratio of compound 19b was determined by chiral HPLC of the corresponding phenylurea and was found to be 89/11. T.l.c. DCM:MeOH (99:1), Rf=0.36. IR: 1709 and 1672 (C═O); 1597 (C═C) cm$^{-1}$. $^1$H NMR: 7.43 (dd); 7.4–7.14 (m); 6.95 (dd); 4.46 (m); 4.28 (s); 3.69 (m); 2.2 (m); 1.9–1.4 (m); 1.3–1.0 (m).

INTERMEDIATE 20

Acetic acid, 3-(tetrazolyl)-anilinium salt

Sodium azide (4.3 g) and ammonium chloride (3.53 g) were added to a solution of 3-aminobenzonitrile (2.6 g) in dry DMF (80 ml) and the mixture was heated at 100° for 18 h. Inorganic materials were filtered off and the filtrate was concentrated in vacuo to a residue, which was taken up in water (100 ml) and acidified with glacial acetic acid until pH=4. The solution was then stirred at 0° C. for 1 h; the yellow precipitate formed was filtered, washed with water and diethyl ether, then dried, to give the title compound (2.73 g) as a yellow solid. T.l.c. DCM:MeOH (8:2), Rf=0.30.

EXAMPLE 1

N-[2,3,4,5-Tetrahydro-1-(3-methylbutyl)-2,4-dioxo-5-phenyl-1H-1,5-benzodiazepin-3-yl]-N'-[3-(1H-tetrazol-5-yl)phenyl]urea TEA (0.084 ml) was added to a stirred solution of 3-(1H-tetrazol-5-yl) benzenamine hydrochloride (119 mg) and N-[2,3,4,5-Tetrahydro-1-(3-methylbutyl)-2,4-dioxo-5-phenyl-1H-1,5-benzodiazepin-3-yl-1H-imidazole-1-carboxamide. (200 mg) in dry THF (5 ml) at 23° under nitrogen and the mixture was heated to reflux for 2 days. The cooled mixture was poured into 0.33N HCl and was extracted with EA. The combined organic extracts were washed with saturated brine, dried and evaporated. The residue was triturated with MeOH then chromatographed with MeOH-DCM (5%–10%) to give the title compound (75 mg) as a white powder, m.p. 220°–222°.

T.l.c. MeOH-DCM (1:9) Rf 0.33 d (DMSO) 0.8–1.0 (6H,m); 1.25–1.65 (3H,m); 3.7–4.0 (1H,m); 4.4.–4.6 (1H, m); 5.05 (1H,d); 6.9–7.9 (13H,m); 8.2 (1H,S); 9.45 (1H,s).

EXAMPLE 2

N-[3-(1H-tetrazol-5-yl)phenyl]-N'-(2,3,4,5-tetrahydro-2,4-dioxo-1-methyl-5-phenyl-1H-1,5-benzodiazepin-3-yl)urea N-(3-cyanophenyl)-N'-(2,3,4,5-tetrahydro-2,4-dioxo-1-methyl-5-phenyl-1H-1,5-benzodiazopin-3-yl)urea (260 mg) was suspended in tributyltin azide (4 g) under nitrogen, and the mixture heated at 160° for 2 h. The cooled mixture was poured into dilute sodium hydroxide solution washed with DE, the aqueous layer acidified using 2M HCl acid to pH1 , extracted with EA: MeOH (10:1 ) dried and the solvent removed in vacuo to leave a yellow solid. Trituration with EA gave the title compound (49mg) as a white solid m.p. 226°–229° (dec).

T.l.c. DCM-MeOH (10:1) R.f.0.40 .

EXAMPLE 3

N-[1-(3,3-Dimethylbutyl)-2,4-dioxo-5-phenyl-2,3,4,5-tetrahydro-1H-1,5-benzodiazepine-3-yl]-N'[3-(5-tetrazolyl)-phenyl]urea 5-(3-Aminophenyl)-tetrazole (0.058 g) and the intermediate 12 (0.100 g) were added to a solution of triethylamine (0.026 g) in dry acetonitrile (6 ml) under a nitrogen atmosphere. The mixture was stirred for 20 hrs, then concentrated "in vacuo". DCM (50 ml) and water (30 ml) were added and the aqueous layer was extracted with DCM (2×30 ml). The combined organic layers were dried and concentrated "in vacuo", dissolved in EA and the desired product was precipitated with petrol. This product was recrystallised from DCM petrol to give the title compound as a white solid (0.075 g).

T.l.c. DMC-MeOH (80:20), Rf=0.44, IR:3310(NH), 1691, 1657, 1641 (C═O)(C═N)cm$^{-1}$;

$^1$H-NMR: 9.46(s), 8.16(bs), 7.78(dd), 7.58(dt), 7.52–7.28 (m), 7.21(d), 7.01(m), 5.04(d), 4.38(m), 3.83(m), 1.40(t), 0.92(s).

EXAMPLE 4

(+)-N-[1-(Cyclopentylethyl)-2,4-dioxo-5-(2-fluorophenyl)-2,3,4,5-tetrahydro-1H-benzodiazepin-3-yl]-N'-(3-tetrazolyl)phenylurea Triphosgene (0.209 g) and, after 5 min., TEA (0.874 ml) were added to a solution of intermediate 20 (0.460 g) in dry THF (50 ml), at 0° C. and under a nitrogen atmosphere. The mixture was allowed to warm to 23° and stirred for 5 min; then, it was cooled again to 0°. Intermediate 19a (0.553 g), dissolved in dry THF (20 ml), was cannulated into this solution and stirring was continued at 0° for 5 more min. The mixture was allowed to warm to 23°, stirred for 3 h, then filtered and concentrated in vacuo. The residue was taken up in ethyl acetate (100 ml), washed with a 5% citric acid solution (2×50 ml) and brine (50 ml), dried and concentrated in vacuo. The residue was triturated with diethyl ether, washed with dichloromethane, filtered and dried, to give the title compound as a white solid (0.137 g). M.p.223°–6°. T.l.c. DCM-MeOH 9:1, $R_f$ 0.53. αD=+104.8°. IR: 3330–3200 (NH), 1697, 1664 and 1637 (C=O, C=N); 1595 (C=C) cm$^{-1}$. $^1$H-NMR: 9.46 (bs); 8.19 (bs); 7.79 (dd); 7.62–7.28 (m); 7.06 (d); 7.02 (dd); 5.10 (d); 4.38 (m); 3.81 (m); 1.82–1.62 (m); 1.60–1.36 (m); 1.16–1.00 (m).

EXAMPLE 5

(−)-N-[1-(Cyclopentylethyl)-2,4-dioxo-5-(2-fluorophenyl)-2,3,4,5-tetrahydro-1H-benzodiazepin-3-yl]-N'-(3-tetrazolyl)phenylurea Triphosgene (0.0545 g) and, after 5 min., TEA (0.223 ml) were added to a solution of intermediate 20 (0.117 g) in dry THF (13 ml), at 0° C. and under a nitrogen atmosphere. The mixture was allowed to warm to 23° C. and stirred for 15 min; then, it was cooled again to 0° C. Intermediate 19a (0.140 g), dissolved in dry THF (5 ml), was cannulated into this solution and stirring was continued at 0° C. for 15 more min. The mixture was allowed to warm to 2320 C., stirred for 1 h and 30 min, then filtered and concentrated in vacuo. The residue was taken up in ethyl acetate (100 ml), washed with a 5% citric acid solution (2×25 ml) and brine (25 ml), dried and concentrated in vacuo. The residue was triturated with diethyl ether, washed with dichloromethane, filtered and dried, to give the title compound as a white solid (0.057 g). M.p.228°–30° C. T.l.c. DCM-MeOH 9:1, $R_f$ 0.53. αD=−82.7°. IR: 3330–3200 (NH), 1697, 1664 and 1637 (C=O, C=N); 1595 (C=C) cm$^{-1}$. $^1$H-NMR: 9.46 (bs); 8.19 (bs); 7.79 (dd); 7.62–7.28 (m); 7.06 (d); 7.02 (dd); 5.10 (d); 4.38 (m); 3.81 (m); 1.82–1.62 (m); 1.60–1.36 (m); 1.16–1.00 (m).

Pharmacy Example

Capsules or Tablets

|  | mg/dosage form |
|---|---|
| Active ingredient | 0.1 |
| Polyethyleneglycol | 15.0 |
| Lactose | 52.4 |
| Starch | 30.0 |
| Magnesium stearate | 0.5 |
| Silicon dioxide | 1.0 |
| Sodium Lauryl Sulphate | 1.0 |
|  | 100.0 |

The active ingredient is dispersed in a suitable solvent (e.g. ethanol) together with polyethyleneglycol. The solvent is removed. The powder so obtained is blended with the other excipients. The blend can be used to fill gelatine capsules or compressed using appropriate punches. The tablets can be coated using conventional techniques and coatings.

| Active ingredient | 0.1 |
|---|---|
| Povidone | 15.4 |
| Lactose | 74.0 |
| Hydrogenated vegetable oils | 3.0 |
| Silicon dioxide | 1.0 |
| Sodium Laauryl sulphate | 1.5 |
| Crospovidone | 5.0 |
|  | 100.0 |

The active ingredient is dispersed in a suitable solvent (e.g. ethanol) together with povidone. The solution is sprayed on to lactose and the solvent removed. The powder obtained is blended with the other excipients. The blend is used to fill gelatine capsules or compressed using appropriate punches. The tablet can be coated using conventional techniques and coatings.

Oral liquid

| Active ingredient | 70–100 micrograms/dose |
|---|---|
| ethanol | 5–15% |
| Sodium saccharinate | 0.1–1% |
| Propylene glycol | q.b. 100% |

Injection Formulation

| Active ingredient | 0.1–100 microgramms |
|---|---|
| Sodium phosphate | 1.50 mg/ml |
| NaOH | qs desired pH (range 3–9) |
| glyerol | 10–500 mg/ml |
| water for injection | qs to 0.5–10 ml |

Pack in glass (ampules) with a rubber stopper (vials, syringes) and a plastic/metal overseal (vials only). An inert gas atmosphere (for example nitrogen) may be introduced into dead space of container.

CCK-Receptor Binding

The binding affinity of the compounds of the invention for the CCK-A receptor (Pancreas Assay) and CCK-B receptor (guinea pig cortex assay) was determined using the procedure of G Dal Forno et al J. Pharmacol. Exp & Ther. 261-1056–1063. The pKi values determined with respresentative compounds of invention were as follows:

|  | pKi | |
|---|---|---|
| Compound Ex No | CCK-A | CCK-B |
| 3 | 7.64 | 9.54 |
| 4 | 6.63 | 9.98 |
| 5 | 6.51 | 9.57 |

The compounds of the invention are essentially non-toxic and therapeutically useful doses.

We claim:
1. A compound of formula (I)

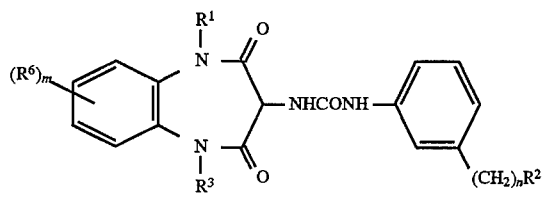

wherein
- $R^1$ represents a phenyl, $C_{3-7}$cycloalkyl, $C_{7-11}$ bridged cycloalkyl or $C_{1-6}$alkyl group which alkyl group may be substituted by a hydroxy, phenyl, $C_{1-6}$-alkoxycarbonyl, $C_{3-7}$cycloalkyl or $C_{7-11}$ bridged cycloalkyl group;
- $R^2$ represents $NR^4SO_2CF_3$, $SO_2NR^4COR^5$, $CONR^4SO_2R^5$, or a tetrazole, carboxamidotetrazole, or 3-trifluoromethyl-1,2,4-triazole group which groups may be substituted on one of the nitrogen atoms by a $C_{1-4}$alkyl group;
- $R^3$ is phenyl optionally substituted by one or two halogen atoms;
- $R^4$ represents hydrogen or a $C_{1-4}$alkyl group;
- $R^5$ represents a $C_{1-4}$alkyl group;
- $R^6$ represents hydrogen or a halogen atom; m is zero, 1 or 2;
- n is zero or 1; and pharmaceutically acceptable salts and solvates thereof.

2. A compound as claimed in claim 1 wherein $R^1$ represents 3-methylbutyl, 3,3-dimethylbutyl or cyclopentylethyl.

3. A compound as claimed in claim 1 wherein $R^2$ represents 1H-tetrazol-5-yl.

4. A compound as claimed in claim 1 wherein $R^3$ represents phenyl or 2-fluorophenyl.

5. A compound as claimed in claim 1 wherein $R^6$ represents hydrogen.

6. A compound as claimed in claim 1 wherein n is zero.

7. A compound selected from:
N-[1-(Cyclopentylethyl)-2,4-dioxo-5-(2-fluorophenyl)-2,3,4,5-tetrahydro-1H-benzodiazepin-3-yl]-N'-(3-tetrazolyl)phenylurea;

N-[2,3,4,5-Tetrahydro-1-(3-methylbutyl)-2,4-dioxo-5-phenyl-1H-1,5-benzodiazepin-3-yl]-N'-[3-(1H-tetrazol-5-yl)phenyl]urea;

N-[1-(3,3-Dimethylbutyl)-2,4-dioxo-5-phenyl-2,3,4,5-tetrahydro-1H-1,5-benzodiazepine-3-yl]-N'[3-(5-tetrazolyl)-phenyl]urea, enantiomers and salts thereof.

8. A pharmaceutical composition comprising an effective amount of a compound as defined in claim 1, in admixture with one or more physiologically acceptable carriers or excipients for the treatment of conditions where modification of the effects of gastrin and/or CCK is of therapeutic benefit.

9. A method of treatment of a mammal including man for conditions where modification of the effects of gastrin and or CCK is of therapeutic benefit comprising administration of an effective amount of a compound as defined in claim 1.

10. A process for the preparation of a compound as defined in claim 1 which comprises:
(a) reacting a compound of formula (II) in which X represents the group $N=C=O$ or $NHCOR^8$ wherein $R^8$ is phenoxy or a 1-imidazole group

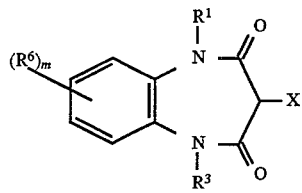

with an amine of formula (III)

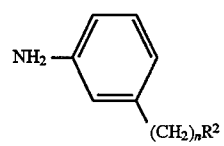

(b) reacting the amine (IV) wherein $R^1$, $R^3$, $R^6$ and m have the meanings defined in formula (I).

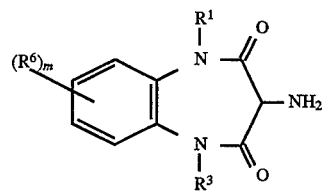

with the isocyanate of formula (V)

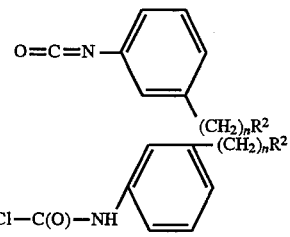

or carbamoyl chloride of formula (VI) or with triphosgene and the amine of formula (III);
and thereafter if necessary or desired separation of a compound of formula (I) into its stereochemical enantiomers thereof.

* * * * *